(12) United States Patent
Ranganathan et al.

(10) Patent No.: US 7,799,967 B2
(45) Date of Patent: Sep. 21, 2010

(54) DIFFERENTIALLY EXPANDING ABSORBENT STRUCTURE

(75) Inventors: Sridhar Ranganathan, Suwanee, GA (US); Fred R. Radwanski, Stone Mountain, GA (US); Jenny L. Day, Woodstock, GA (US); Jeffrey J. Krueger, Marietta, GA (US); Gregory M. Lefkowitz, Gainesville, FL (US); Stanley R. Kellenberger, Appleton, WI (US); Hoa La Wilhelm, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 158 days.

(21) Appl. No.: 10/820,636

(22) Filed: Apr. 8, 2004

(65) Prior Publication Data
US 2005/0228350 A1    Oct. 13, 2005

(51) Int. Cl.
*A61F 13/15* (2006.01)
*A61F 13/20* (2006.01)

(52) U.S. Cl. .......... 604/369; 604/367; 604/368
(58) Field of Classification Search .......... 604/378, 604/381–383, 385.01, 367–369
See application file for complete search history.

(56) References Cited

U.S. PATENT DOCUMENTS

| | | | |
|---|---|---|---|
| 2,532,241 A * | 11/1950 | Ott ........................ | 521/89 |
| 2,993,013 A | 7/1961 | Wolfe et al. | |
| 3,306,795 A | 2/1967 | Morse | |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,563,243 A | 2/1971 | Lindquist | |
| 3,692,618 A | 9/1972 | Dorschner et al. | |
| 3,741,388 A * | 6/1973 | Takahashi ............... | 210/770 |
| 3,802,817 A | 4/1974 | Matsuki et al. | |
| 3,805,532 A | 4/1974 | Kistner | |
| 3,849,241 A | 11/1974 | Butin et al. | |

(Continued)

FOREIGN PATENT DOCUMENTS

EP    0 650 714 A1    5/1995

(Continued)

OTHER PUBLICATIONS

English translation of JP 2003-033381 A.*

(Continued)

*Primary Examiner*—Melanie J Hand
(74) *Attorney, Agent, or Firm*—Armstrong Teasdale, LLP

(57) ABSTRACT

An absorbent structure expands to a greater extent along one surface than along an opposite surface when in the presence of a liquid. The absorbent structure may include a single layer, or two or more layers intimately bonded to one another. When in the presence of a liquid, the more expandable surface causes an increase in concavity in the X-Y plane of the structure, with the concavity being in the direction of the less expandable surface. One or both surfaces can be treated to adjust the respective level of expandability. By inducing a formed shape upon hydration swelling, a trough shape can be generated to facilitate absorbent properties, containment, and fit. The invention includes absorbent articles having such an absorbent structure incorporated therein.

40 Claims, 7 Drawing Sheets

U.S. PATENT DOCUMENTS

| | | | |
|---|---|---|---|
| 4,098,728 | A * | 7/1978 | Rosenblatt .................. 521/141 |
| 4,137,200 | A | 1/1979 | Wood et al. |
| 4,209,605 | A | 6/1980 | Hoy et al. |
| 4,340,563 | A | 7/1982 | Appel et al. |
| 4,447,240 | A | 5/1984 | Ito et al. |
| 4,668,230 | A | 5/1987 | Damico et al. |
| 4,794,034 | A | 12/1988 | Nishizawa et al. |
| 4,822,668 | A | 4/1989 | Tanaka et al. |
| 4,931,005 | A | 6/1990 | Tanaka et al. |
| 4,939,016 | A | 7/1990 | Radwanski et al. |
| 4,950,264 | A * | 8/1990 | Osborn, III ............ 604/385.08 |
| 4,990,541 | A | 2/1991 | Nielsen et al. |
| 5,197,959 | A | 3/1993 | Buell |
| 5,246,431 | A | 9/1993 | Minetola et al. |
| 5,300,055 | A | 4/1994 | Buell |
| 5,328,450 | A | 7/1994 | Smith et al. |
| 5,336,545 | A | 8/1994 | Morman |
| 5,350,371 | A * | 9/1994 | Van Iten .................. 604/378 |
| 5,374,260 | A | 12/1994 | Lemay et al. |
| 5,454,802 | A * | 10/1995 | Lindquist et al. ....... 604/385.05 |
| 5,460,621 | A * | 10/1995 | Gertzman et al. ........... 604/358 |
| 5,466,232 | A | 11/1995 | Cadieux et al. |
| 5,531,730 | A | 7/1996 | Dreier |
| 5,545,156 | A | 8/1996 | Di Palma et al. |
| 5,558,660 | A | 9/1996 | Dreir |
| 5,560,878 | A | 10/1996 | Dragoo et al. |
| 5,591,150 | A * | 1/1997 | Olsen et al. ............ 604/385.23 |
| 5,591,779 | A | 1/1997 | Bleys et al. |
| 5,601,544 | A | 2/1997 | Glaug et al. |
| 5,624,421 | A * | 4/1997 | Dabi et al. .................. 604/378 |
| 5,676,661 | A | 10/1997 | Faulks et al. |
| 5,688,259 | A | 11/1997 | Osborn, III et al. |
| 5,753,076 | A | 5/1998 | Costello et al. |
| 5,776,122 | A | 7/1998 | Faulks et al. |
| 5,797,894 | A | 8/1998 | Cadieux et al. |
| 5,827,258 | A | 10/1998 | McFall et al. |
| 5,853,403 | A | 12/1998 | Tanzer et al. |
| 5,858,292 | A | 1/1999 | Dragoo et al. |
| 5,947,947 | A | 9/1999 | Tanzer et al. |
| 5,957,909 | A | 9/1999 | Hammons et al. |
| 5,961,506 | A | 10/1999 | Guidotti et al. |
| 6,020,536 | A | 2/2000 | Osterdahl et al. |
| 6,037,518 | A | 3/2000 | Guidotti et al. |
| 6,162,204 | A | 12/2000 | Romare |
| 6,198,019 | B1 * | 3/2001 | Hansson et al. ............. 604/378 |
| 6,362,389 | B1 | 3/2002 | McDowall et al. |
| 6,406,648 | B1 | 6/2002 | Noel et al. |
| 6,447,496 | B1 | 9/2002 | Mizutani |
| 6,492,574 | B1 | 12/2002 | Chen et al. |
| 6,596,387 | B2 | 7/2003 | Ogle |
| 6,667,424 | B1 * | 12/2003 | Hamilton et al. ............. 604/375 |
| 2005/0096619 | A1 * | 5/2005 | Costa .................... 604/385.17 |

FOREIGN PATENT DOCUMENTS

| | | |
|---|---|---|
| EP | 0 794 751 B1 | 9/1997 |
| EP | 0 804 915 | 11/1997 |
| EP | 804915 A1 * | 11/1997 |
| EP | 0 880 955 | 12/1998 |
| EP | 1 079 786 B1 | 8/2002 |
| WO | WO 91/11161 | 8/1991 |
| WO | WO 98/00084 | 1/1998 |
| WO | WO 99/25284 | 5/1999 |
| WO | WO 00/00127 | 1/2000 |
| WO | WO 01/15649 | 3/2001 |
| WO | WO 01/25390 A2 | 4/2001 |
| WO | WO 01/26592 A1 | 4/2001 |
| WO | WO 01/80916 A2 | 11/2001 |
| WO | WO 03/009791 | 2/2003 |

OTHER PUBLICATIONS

Cellular Rooting Sponge® Technology, *Grow-Tech Inc.*, 1999.
*Medical Foam*, Rynel® Foam Follows Function, 1997.

* cited by examiner

DIFFERENTIALLY EXPANDING ABSORBENT STRUCTURE

BACKGROUND OF THE INVENTION

This invention is directed to absorbent structures, including one or more layers having differential swelling characteristics, which through controlled curvature can transform a flat planar material into one having desired shaping. The invention is also directed to absorbent articles incorporating such absorbent structures.

Absorbent articles typically include one or more absorbent layers capable of absorbing and retaining liquids. Some absorbent articles include a surge layer that is capable of quickly absorbing liquid, but is unable to retain a large quantity of liquid. A second absorbent layer having a higher absorbent capacity than a surge layer is typically located below the surge layer such that the surge layer quickly intakes liquid and subsequently passes the liquid to the more absorbent layer to retain the liquid. However, when a flat absorbent layer, such as a surge layer or a higher absorbent capacity layer, becomes saturated or is loaded too rapidly, excess liquid is likely to run off the layer in virtually any direction.

Additional components are often included in absorbent articles to further prevent the leakage of fluids from the articles. For example, certain personal care products, such as training pants, incontinence products, and diapers, often include containment flaps around the leg openings to prevent leakage at the leg openings. However, containment flaps are generally not absorbent, thus leaving the liquid free to migrate into other areas of the garment.

Molded absorbent layers are known. For example, foams may be molded into a cup-like shape, thereby directing the flow of liquid into the cup area to avoid liquid run-off. SERENITY® Guards feminine incontinence product, available from McNeil-PPC, Inc., a Johnson & Johnson Company, Milltown, N.J., U.S.A., is an example of a molded, yet non-absorbent shaped foam. However, molded foams are typically bulky and lack flexibility, thereby causing discomfort to the wearer.

There is thus a need or desire for an absorbent material that is thin and flexible in a dry state, and forms a three-dimensional concave shape when the material is sufficiently wetted, thereby directionalizing fluid flow to enhance the material's liquid-containment capability. With the concave shape, runny BM handling can be improved along with skin wellness since the concavity may be designed to create separation between the skin and the bulk of the contained fluid or BM.

SUMMARY OF THE INVENTION

This invention is directed to absorbent structures that are thin and flexible in a dry state and, when sufficiently wetted, form a three-dimensional concave shape. The invention also includes absorbent articles including such absorbent structures.

The absorbent structures of the invention include one or more layers that, in the absence of a liquid, may be thin and flexible enough to lie flat. Suitably, the absorbent structure may have a thickness of about 10 millimeters or less in a dry state. In a single-layer embodiment, one surface of the structure possesses differential swelling behavior in the presence of a liquid compared to the opposite surface of the structure.

In a multi-layer embodiment, at least a first layer and a second layer are laminated together such that they remain attached to one another even when wet. Suitably, one or both of the layers is absorbent. In the presence of a liquid, the second layer expands to a greater extent than the first layer, thereby causing increased concavity along an interface of the two layers, with the concavity directed toward the first layer. For example, the first layer may expand less than 10% in the presence of a liquid, while the second layer may expand at least 20% in the presence of a liquid. The first and/or second layers may expand either isotropically or anisotropically. The absorbent structure suitably has a fluid intake rate of about 0.5 cubic centimeters per second (cc/s) or greater.

In the expanded or swollen state, the absorbent structure suitably has a subtended angle of concavity of about 180 degrees or less, and a radius of curvature of about 38 centimeters or less. The subtended angle and the radius of curvature can either be measured when the material is in the swollen state, or can be calculated from measurements taken on the individual layers apart from the absorbent structure.

The concave shape of the structure may be controlled in several different ways. These controlling factors of the layers and/or surfaces include the basis weights, the thickness, the different moduli of the layers and/or surfaces, the properties of the layers or surfaces in the dry state as well as in the wet state, orientation and type of structural components, level and type of superabsorbent add-on in one or more layers/surfaces, the inclusion of heterogeneous features such as folds, slits, or other cuts in the individual layers or surfaces to profile the shape and/or facilitate rapid fluid movement through the layer or surface, and/or bonding of the structure to a secondary relatively fixed member such as an outer cover of a personal care absorbent article. The concave shape may also be controlled by reducing expansion in at least one region of at least one of the layers by using such techniques as densification, embossment, heat treatment, or bonding, including mechanical or hydraulic needling, or adhesive, ultrasonic, or thermal bonding. Furthermore, expansion differentials between the two layers, within a single layer, can be engineered by treating the first layer or first surface to expand less relative to the extent to which the second layer or second surface expands. Such treatments may include necking, creping, aperturing, mechanical teasing, and/or pleating of the layer(s).

The first layer may include nonwoven materials, wetlaid, airlaid, spunbond, meltblown, coform, bonded-carded webs, foam, tissue, netting, including scrim and woven materials, or a combination of any of these materials. The second layer, or a single-layer embodiment, may include thermoplastic hydrophilic foam, thermoset hydrophilic foam, cellulosic foam, superabsorbent foam, foam materials with superabsorbent particles embedded therein, non-foam materials with superabsorbent particles embedded therein, fibrous materials, such as cellulose, staple fibers, and/or airlaid, with superabsorbent particles embedded therein, coforms, staple fiber webs, nettings and scrims, superabsorbent scrims, superabsorbent films, spunbond with superabsorbents, meltblown with superabsorbents, or a combination of any of these materials. Superabsorbent material may be included in one or both layers. The second layer materials must be expandable upon exposure to liquid. Additionally, one or more of the layers may be elastomeric. The layers may be bonded together using chemical, adhesive, or thermal or hydraulic or mechanical bonding, for example.

The absorbent structures of the invention can be included in absorbent articles, such as diapers, training pants, swimwear, absorbent underpants, other disposable garments, adult incontinence products including but not limited to pads, containers, incontinence products, and urinary shields, feminine hygiene products including but not limited to sanitary napkins, menstrual pads, panty liners, panty shields, interlabials, tampons, medical absorbent garments, drapes, gowns, bandages, wound dressings, underpads, bed pads, cleaning applications, clothing components, filters, athletic and recreation products, construction products, packaging products, and the like. In personal care absorbent articles, for example, the three-dimensional configuration of the absorbent structure in the wet state is a cup-like or bucket-like configuration that enhances fluid as well as solid containment, thus keeping such bodily discharges away from a wearer's skin, thereby improving comfort and skin health.

With the foregoing in mind, it is a feature and advantage of the invention to provide an absorbent structure that is thin and flexible in a dry state, and forms a three-dimensional concave shape in the presence of a liquid.

BRIEF DESCRIPTION OF THE DRAWINGS

These and other objects and features of this invention will be better understood from the following detailed description taken in conjunction with the drawings, wherein.

DEFINITIONS

Figure 1:
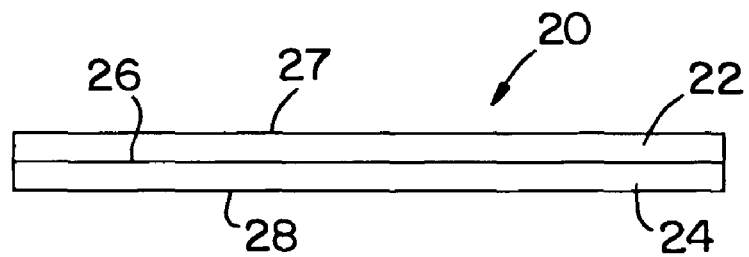
FIG. 1 is a side view of an absorbent structure in a dry state.

Within the context of this specification, each term or phrase below will include the following meaning or meanings.

"Airlaid" refers to a material produced by forming previously individualized fibers with or without other materials and bonding them together with adhesives, glues, and/or heat-activated binder fibers.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Cellulose fibers" refers to fibers from natural sources such as woody and non-woody plants, regenerated cellulose, and derivatives from these fibers by means of chemical, mechanical or thermal treatment, or any combination of these. Woody plants include, for example, deciduous and coniferous trees. Non-woody plants include, for instance, cotton, flax, esparto grass, milkweed, straw, jute hemp, and bagasse. Regenerated cellulose fibers include, for instance, viscose and rayon. The cellulose derivatives include, for instance, microcrystalline cellulose, chemically crosslinked fibers, and chemically uncrosslinked, twisted fibers.

"Coform" is a composite material that is essentially an air-formed matrix of thermoplastic polymer microfibers, including meltblown fibers, and a multiplicity of individualized cellulose and/or staple fibers and/or particulates such as superabsorbents disposed throughout the matrix of microfibers and engaging at least some of the microfibers to space the microfibers to intertwine and hold captive within the matrix of microfibers by mechanical entanglement of the microfibers with the cellulose and/or staple fibers and/or particulates including superabsorbent.

"Elastomeric" and "elastic" are used interchangeably to refer to a material or composite having rubbery properties that is generally capable of recovering its shape after deformation when the deforming force is removed. Specifically, as used herein, elastic or elastomeric is meant to be that property of any material which, upon application of an elongating force, permits the material to be stretchable to a stretched length which is at least about 25 percent greater than its relaxed length; and that will cause the material to recover at least 40 percent of its elongation upon release of the stretching elongating force. A hypothetical example which would satisfy this definition of an elastomeric material would be a one (1) inch (2.5 cm) sample of a material which is elongatable to at least 1.25 inches (3.2 cm) and which, upon being elongated to 1.25 inches (3.2 cm) and released, will recover to a length of not more than 1.15 inches (2.9 cm). Many elastomeric materials may be stretched by much more than 25 percent of their relaxed length, and many of these will recover to substantially their original relaxed length upon release of the stretching elongating force. In addition to a material being elastomeric in the aforementioned X-Y planar dimensions of a structure, including a web or sheet, the material may also be elastomeric in the Z planar dimension. Specifically, when compression is applied to an elastomeric structure, the structure may display elastomeric properties and then recover to near its original position upon relaxation. The elastic property can both form and retain the curvature shape of the absorbent structure with fluid and BM loading and with compression loading and unloading forces.

"Expand" includes not only expansion by volume, but also extension through elastomeric and stretchable planar dimension properties.

"Hydrophilic" describes surfaces and fibers, or the surfaces of fibers, which have a high affinity for aqueous liquids and are wetted by the aqueous liquids when in contact with the surfaces. The degree of wetting of the materials can, in turn, be described in terms of the contact angles and the surface tensions of the liquids and materials involved. Equipment and techniques suitable for measuring the wettability of surfaces on particular fiber materials or blends of fiber materials can be provided by a Cahn SFA-222 Surface Force Analyzer System available from Thermo Electron Corporation in Madison, Wis., U.S.A., or a substantially equivalent system. When measured with this system, fibers or surfaces having contact angles of less than 90° are designated "wettable" or hydrophilic, while fibers or surfaces having contact angles greater than 90° are designated "nonwettable" or hydrophobic.

"In the presence of a liquid" refers to physical contact with a liquid that provides sufficient wetting to cause an expandable material to expand to the extent that the material would expand when saturated.

"Liquid" refers to fluids that are expected to be encountered in routine use of articles of the invention such as urine, menses, BM, saline, water, blood, sweat, and the like.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al., which is hereby incorporated by reference in its entirety in a manner consistent with the present document. Meltblown, fibers are microfibers which may be continuous or discontinuous, are generally smaller than about 0.6 denier, and are generally self-bonding when deposited onto a collecting surface.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded-carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is hereby incorporated by reference in its entirety in a manner consistent with the present document. Spunbond fibers are quenched and generally not tacky when they are deposited onto a collecting surface. Spunbond fibers are generally continuous and often have average deniers larger than about 0.3 denier, more particularly, between about 0.6 and 10 denier.

"Staple fibers" means filaments or fibers which are natural or which are cut from a manufactured filament prior to forming into a web, and which have a length ranging from about 0.1-15 cm, more commonly about 0.2-7 cm. Such fibers maybe bonded into a bonded-carded web.

"Superabsorbent" refers to a water-swellable, water-insoluble organic or inorganic material, spontaneous hydrogel, capable under the most favorable conditions of absorbing at least about 10 times its own weight, or at least about 15 times its own weight, or at least about 20 times its own weight, or at least about 25 times its own weight of an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. A material is "absorbent" if it absorbs at least five times its weight of a 0.9% sodium chloride aqueous solution under these conditions.

"Thermoplastic" is meant to describe a material that softens and/or flows when exposed to heat and which substantially returns to its original hardened condition when cooled to room temperature.

"Thermoset" is meant to describe a material that is capable of becoming permanently cross-linked, and the physical form of the material cannot be changed by heat without the breakdown of chemical bonds.

"Personal care absorbent article" includes, but is not limited to, absorbent articles such as disposable diapers, training pants, child-care pants, swim wear, absorbent underpants, nursing pads, adult incontinence products including pads, incontinence products, and urinary shields, feminine hygiene products including sanitary napkins, menstrual pads, panty liners, panty shields, interlabials, and the like.

"Medical absorbent article" includes medical absorbent garments, drapes, gowns, bandages, wound dressings, underpads, filters, containers, bed pads, and the like.

These terms may be defined with additional language in the remaining portions of the specification.

DESCRIPTION OF PREFERRED EMBODIMENTS

In accordance with the invention, an absorbent structure that is thin and flexible in a dry state, and forms a three-dimensional concave shape in the presence of a liquid, can be included in a variety of absorbent articles. The absorbent structure includes one or more layers of materials, or surfaces of material(s), having different in-plane swelling characteristics when exposed to a sufficient amount of liquid. The absorbent structure may be two-dimensional, or flat, when in a dry state, or alternatively may exhibit a small degree of three-dimensional concavity in a dry state, and in a wet state the differential swelling characteristics of the layer(s) leads to either the formation of a three-dimensional concave shape or increased concavity of the three-dimensional shape of the absorbent structure.

For purposes of simplification, a two-layer absorbent structure 20, as shown in FIG. 1, is used herein to illustrate the invention. It should be understood that the overall configurations of the absorbent structures 20 illustrated herein may also be achieved using a single layer or more than two layers in accordance with the invention. In each embodiment of the invention, the absorbent structure 20 has a first surface and a second surface opposite the first surface. When the absorbent structure 20 is essentially a single layer, the first and second surfaces are the top and bottom, or opposite surfaces, of the single layer. When the absorbent structure 20 includes two layers, the first surface of the absorbent structure is an exterior surface of the first layer and the second surface of the absorbent structure is the exterior surface of the second layer. Suitably, one or more of the layers is absorbent.

As shown in FIG. 1, the absorbent structure 20 of the invention may include a first layer 22 bonded to a second layer 24. Alternatively, the absorbent structure 20 may include a single layer. In a dry state, such as in FIG. 1, the absorbent structure 20 is sufficiently thin and flexible to allow the absorbent structure 20 to lie flat. Alternatively, in a dry state, the absorbent structure 20 may exhibit some concavity. More particularly, in a dry state, the first layer 22 and the second layer 24 have approximately the same width and length dimensions and are in an essentially internal-stress-free state. Thus, a first surface 27 and a second surface 28 of the absorbent structure opposite the first surface 27 also have approximately the same width and length dimensions. In a dry state, the absorbent structure suitably has an overall thickness between about 1 and about 10, or between about 2 and about 5 millimeters (mm). Furthermore, in a dry state, the absorbent structure 20 is of sufficient softness, hand, and drape, and suitably has a Gurley stiffness of about 600 milligrams (mg) of force or less, or about 300 mg of force or less, or about 150 mg of force or less, or about 50 mg of force or less; and is elastic and resilient with an edge compression of about 250 grams or less, or about 100 grams or less, or about 35 grams or less. Gurley stiffness can be measured using the Gurley Stiffness Test Method, and edge compression can be measured using the Edge Compression Test Method, both of which are described in detail below.

The surface of the absorbent structure 20 that faces a user or is expected to be in contact with liquid during use should have the ability to allow liquid to permeate through the surface at a relatively rapid rate. Thus, the absorbent structure 20 suitably has a fluid intake rate of about 0.5 cubic centimeters per second (cc/s) or greater, or about 1 cc/s or greater, or about 2 cc/s or greater, or about 5 cc/s or greater. The fluid intake rate can be measured using the Fluid Intake Rate Test described in detail below.

Figure 2:
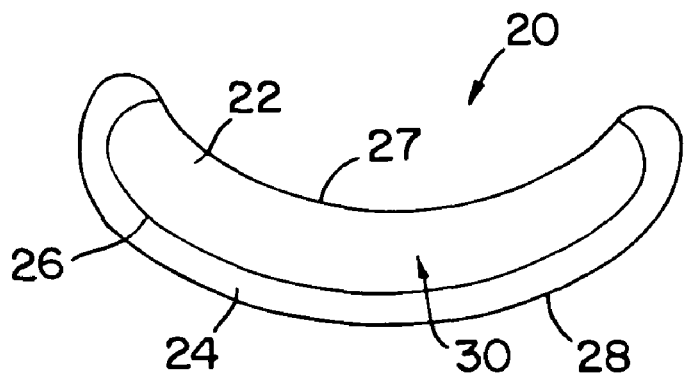
FIG. 2 is a side view of an absorbent structure in a wet, swollen state.

As shown in FIG. 2, when the absorbent structure 20 is in the presence of a sufficient amount of liquid, the first layer 22 (first surface 27) and the second layer 24 (second surface 28) exhibit different swelling characteristics and thereby lead to an unbalanced state-of-stress in the planes of the absorbent structure 20. More particularly, the first layer 22 (first surface 27) expands to a lesser extent than the second layer 24 (second surface 28). In fact, the first layer 22 may not expand at all, or may expand a negligible amount, in certain embodiments. Additionally, the first layer 22, the second layer 24, and/or the absorbent structure 20 may undergo expansion, and the expansion of one or more layers 22, 24 individually, or the absorbent structure 20 as a whole, may be either isotropic or anisotropic. That is, greater expansion may occur in a longitudinal direction as opposed to a transverse direction, or vice-versa. Furthermore, expansion may occur solely in one direction, such as the longitudinal direction or the transverse direction. Alternatively, greater or lesser expansion may occur in a designated target area in either a centered or off-centered location of the absorbent structure 20. As one layer expands, the other layer may expand and/or be stretched.

The differential swelling characteristics between the two surfaces 27, 28 from a dry state to a wet state cause the absorbent structure 20 to deform out-of-plane resulting in an increase in concavity along an interface 26 of the first and second layers 22, 24, with the concavity directed toward the first layer 22 such that a cup-like, bucket-like, pocket-like, trough-like, or other indented-shape or cavity-shape is formed with the first layer 22 on the inside surface of the concave configuration. The area of concavity 30 is particularly suitable for collecting bodily fluids or other bodily wastes for improved absorbency, skin health, and/or fit of absorbent articles.

As an alternative embodiment, rather an alternative function, the absorbent structure 20 can be used upside-down such that the area of concavity 30 faces away from a user. Consequently, from such a perspective, an area of convexity would be directed toward the user. The area of convexity is particularly suitable for providing close body contact, which is beneficial for providing close-to-the-body absorption in such applications as adult incontinence products and feminine care products. In this embodiment, as in the other embodiments herein, the first layer 22 toward which the concavity is directed expands to a lesser extent than the second layer 24. However, in the convex configuration in which the second layer 24 is in closer proximity to the user than the first layer 22, the first layer 22 may possess greater absorbency than the second layer 24. It shall be understood that the term "concavity" is used herein with the understanding that an area of convexity is present along a surface opposite the area of concavity 30.

The out-of-plane deformation, or enhancement of concavity, is a function of many variables including the swelling force exerted by the second surface 28, expansion level, the orientation and type of structural components, the bond strength between the first and second layers 22, 24, the elastic moduli, basis weights, superabsorbent add-on levels and types, and other properties of the first and second layers 22, 24 and/or surfaces 27, 28 in the dry state as well as in the wet state, the inclusion of any heterogeneous features, and the thickness of the first and second layers, 22, 24, among other factors known to those skilled in the art. Additionally, the first layer 22 and/or other layers present in the absorbent structure 20 may shrink when exposed to a sufficient amount of liquid, thus contributing to the out-of-plane deformation.

Figure 3:
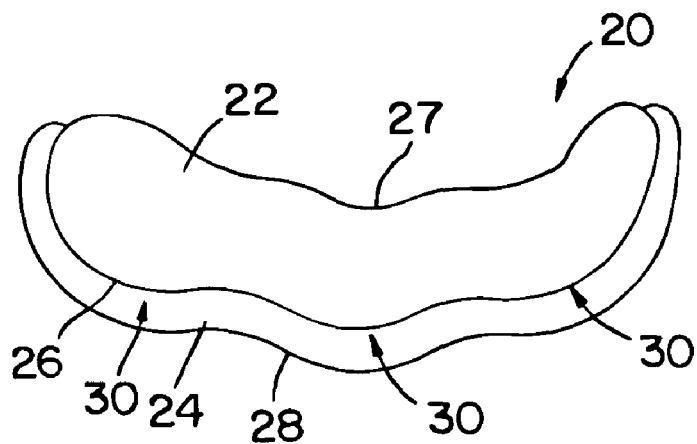
FIG. 3 is a side view of an absorbent structure in a wet, swollen state exhibiting multiple concave regions.

In certain embodiments, the absorbent structure 20 may form more than one area of concavity 30, as illustrated in FIG. 3. For example, the absorbent structure 20 may include multiple discontinuous domains, thereby resulting in multiple areas of concavity 30, or multiple areas of convexity, or a combination of concave and convex areas.

Interface bond strength between the first and second layers 22, 24 is strong enough to keep the first and second layers 22, 24 bonded together in both a dry state and a wet state, even when differential planar swelling forces exist in the first and second layers 22, 24. The absolute magnitude of the interface bond strength depends on the stress exerted by the first and second layers 22, 24 upon one another and is therefore dependent on the particular configuration of the absorbent structure 20. The force acting on the interfacial bond is related to the shear force and total bond area between the first and second layers 22, 24. Therefore, the interfacial bond strength necessary is dependent on the materials used in the absorbent structure and the level of expansion they undergo. The importance of sufficient interface bond strength is demonstrated hypothetically by a scenario in which two materials with different swelling characteristics are merely placed together without bonding between them. In such a case, the separate unbonded materials would behave independently in the presence of a liquid and a single shaped macrostructure would not be formed. This invention recognizes the potential to combine two or more layers into a laminate form that yields a composite providing attributes that neither of the layers individually provides in a wet state.

The absorbent structures 20 can be formed by adhesively bonding the first layer 22 to the second layer 24. Suitable adhesives include hot. melt adhesives, such as Bostik 7109 from Bostik, Inc. of Middleton, Mass., U.S.A. This polyester-based hot melt binder/adhesive has a low fusion temperature and has excellent bonding properties to vinyl, textiles, and foams including polyurethane foams, whether in a wet or dry state. Other suitable adhesives include Bostik PE103, Bostik PE65, and Bostik 7186, each available from Bostik, Inc. of Middleton, Mass., U.S.A. The adhesive may be applied at an add-on between about 10 and about 90 grams per square meter (gsm), or between about 30 and about 70 gsm. With thermoset materials, the bonding may be carried out by positioning the first layer 22 on top of the second layer 24 at the initial stage of curing to allow sufficient integration of the second layer 24 within the first layer 22 for adequate interface bonding to produce high dry and wet laminate bond strength. Alternative types of suitable bonding between layers include chemical bonding, thermal or ultrasonic bonding, fiber entanglement, including mechanical, hydraulic and commingling fibrous webs, and the like. One method of bonding two layers together to form an interfacial bond is to partially merge two fibrous airstreams together to obtain sufficient intermingling and entanglement of the streams within the interfacial region to generate bonding between the two fibrous layers while forming onto a moving foraminous wire. Fibrous airstreams including wood or vegetable fibrous streams, staple fiber streams, meltblown, spunbond, coform streams and combinations thereof can be used to obtain a commingled fibrous interfacial layer between layers 22 and 24. Use of dual dies to obtain partial fiber commingling is described in U.S. Pat. No. 4,939,016 issued to Radwanski et al., which is hereby incorporated by reference in its entirety in a manner consistent with the present document.

The following is a simplified explanation of the deformation behavior of the absorbent structures 20 of the invention. It should be noted that this analysis has been carried out with significant simplifications and assumptions and is, therefore, not intended to limit the scope of the invention. For purposes of this analysis, it is assumed that the first and second layers 22, 24 are flexible enough that the forces due to swelling are sufficient to cause bending of the first and second layers 22, 24. This analysis also applies to other embodiments, including a single-layer embodiment treated for greater or lesser swelling properties along the first surface 27 and/or second surface 28.

Figure 4:
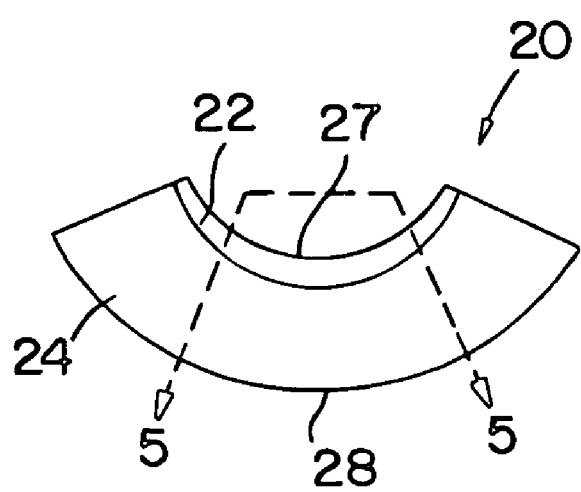
FIG. 4 is a side-view diagram of an absorbent structure in a wet, swollen state.
Figure 5:
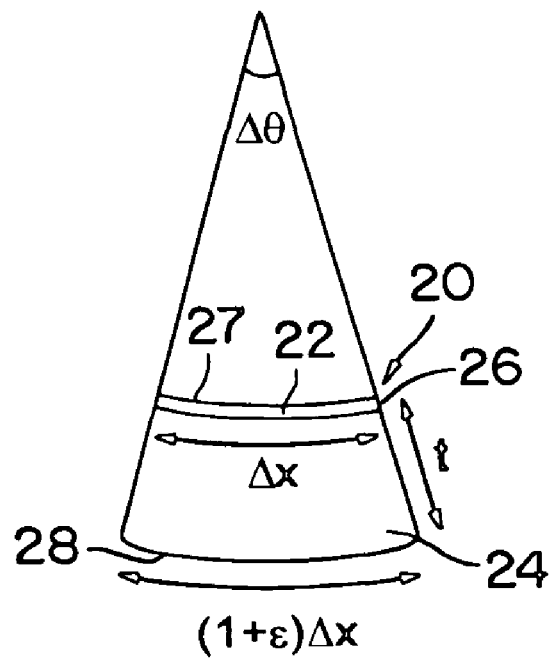
FIG. 5 is a sectional-view diagram of the absorbent structure taken along line 5-5 in FIG. 4, illustrating the dimensions of the absorbent structure in a wet, swollen state.

FIG. 4 is a side-view diagram of the absorbent structure 20 in a swollen state. FIG. 5 is a detailed view of the absorbent structure 20 illustrating the quantitative dimensions of the absorbent structure 20 in a swollen state upon hydration. As shown in FIG. 5, the absorbent structure 20 maintains a length dimension of $\Delta x$ along the interface 26, whereas the second layer 24 expands to a dimension of $(1+\epsilon)\Delta x$ along the second surface 28 opposite the interface 26. Because of the interlaminar bond, the surface of the second layer 24 along the interface 26 is constrained by the first layer 22 and may be subjected to compression due to the bending of the beam, assuming a neutral axis is located within the second layer 24. In order to maintain a simple analysis, it is assumed that the neutral axis coincides with the interface 26. The original (dry state) width of the absorbent structure 20, the first layer 22, the second layer 24, and the interface 26 are all approximately the same. From geometric considerations, it can be shown that the total subtended angle, $\theta$, of the area of concavity 30 of the absorbent structure 20 can be determined in terms of the original width, Wc, of the absorbent structure 20, the fractional change, $\epsilon$, of the width of the surface 28 of the second layer 24 opposite the interface 26, and the wet thickness, t, of the absorbent structure 20, as presented in Equation 1:

$$\theta = \epsilon * Wc/t \qquad (1)$$

From Equation 1, the radius of curvature, R, for the second surface 28 can be expressed as shown in Equation 2:

$$R = Wc*(1+\epsilon)/\theta \qquad (2)$$

The absorbent structures 20 of the invention suitably have a subtended angle, $\theta$, of about 180 degrees or less, or about 150 degrees or less, or about 120 degrees or less. Furthermore, the absorbent structures 20 of the invention suitably have a radius of curvature of about 15 inches (38 cm) or less, or about 10 inches (25 cm) or less, or about 5 inches (13 cm) or less.

The concave shape of the absorbent structure 20 may be controlled in several ways. In one embodiment, the materials chosen for each of the first and second layers 22, 24 may, in themselves, expand to different extents. For instance, the first layer 22 may expand about 10% or less, or about 5% or less, or not at all, in the X and/or Y planar dimensions in the presence of a liquid, while the second layer 24 may expand in the X and/or Y planar dimensions, about 20% or more, or about 40% or more, or about 60% or more, in the presence of a liquid.

In another embodiment, the materials for each of the first and second layers 22, 24 may be chosen based on their basis weights. For example, the first layer 22 may have a basis weight between about 10 and about 150 grams per square meter (gsm) or between about 20 and about 120 gsm, and the second layer 24 may have a basis weight between about 100 and about 1000 gsm, or between about 200 and about 800 gsm. A single-layer absorbent structure may have a basis weight between about 50 and about 1000 gsm, for example.

Additionally, an expansion ratio can be determined to achieve a desired curl arc (radius of curvature). For example, it may be determined that to achieve a desired curl arc the first surface 27 and the second surface 28 must expand in a 1:1.2 ratio. In certain embodiments, it may be determined that the second surface 28 must expand between about 10% and about 80%, or between about 20% and about 70%, more than the first surface 27 expands in the presence of a liquid.

In another embodiment, expansion of the first and/or second surfaces 27, 28 may include not only physical enlargement of the surfaces in the presence of a liquid, but also may include elastomeric properties and stretch properties such as those achieved through such treatments as necking, creping, pleating, aperturing, mechanical teasing, and other methods of altering the dimensions of materials relative to their unprocessed state. One example of a necking process is described in detail in U.S. Pat. No. 5,336,545 issued to Morman, which is hereby incorporated by reference in its entirety in a manner consistent with the present document. One example of a creping process is described in detail in U.S. Pat. No. 5,753,076 issued to Costello et al., which is hereby incorporated by reference in its entirety in a manner consistent with the present document. These treatments are particularly suitable for treating the first layer 22 to expand less than the second layer 24 in the presence of a liquid. More particularly, such treatments can be used to control the elongation-to-stop of spunbond, meltblown, tissue, bonded-carded web, and practically any other materials from which the first layer 22 may be formed. Another example of materials that can be used to achieve differential expansion is the material described in detail in U.S. Pat. No. 6,362,389 issued to McDowall et al., and hereby incorporated by reference in its entirety in a manner consistent with the present document. More particularly, the material in U.S. Pat. No. 6,362,389 may include superabsorbent material in a greater concentration along the second surface 28 than along the first surface 27, such that the second surface 28 would expand more in the presence of a liquid. A subtle concavity present in the dry state can help control the shape and formation of the increased concavity of the absorbent structure 20 in the presence of a liquid.

In yet another embodiment, heterogeneous features, such as slits or other types of apertures, in one or both of the individual first and second layers 22, 24, or in the first or second surfaces 27, 28, can be used to profile the shape of the resulting absorbent structure 20 in the wet concave conformation. For example, one or more slits could be formed in the second layer 24 to create a desirable stress field in the material in order to achieve the desired conformation. The slits can be strategically made in essentially any shape, such as longitudinal slits or geometrical shapes such as a grid, depending on the size of the absorbent structure 20 and its intended use. The dimensions, number, and spacing of the slits may all vary depending on the size of the absorbent structure 20 and its intended use.

Another example of a heterogeneous feature may be in the form of one or more regions of reduced expansion on one or both first and second surfaces 27, 28 and/or layers 22, 24. These regions of reduced expansion may be created by densifying, embossing, heat treating, adhesive bonding, ultrasonic bonding, or any combination of these or other modifications to the first and/or second surfaces 27, 28 and/or layers 22, 24. These regions of reduced expansion, like the slits described above, may be strategically placed to achieve a desirable conformation.

Figure 6:
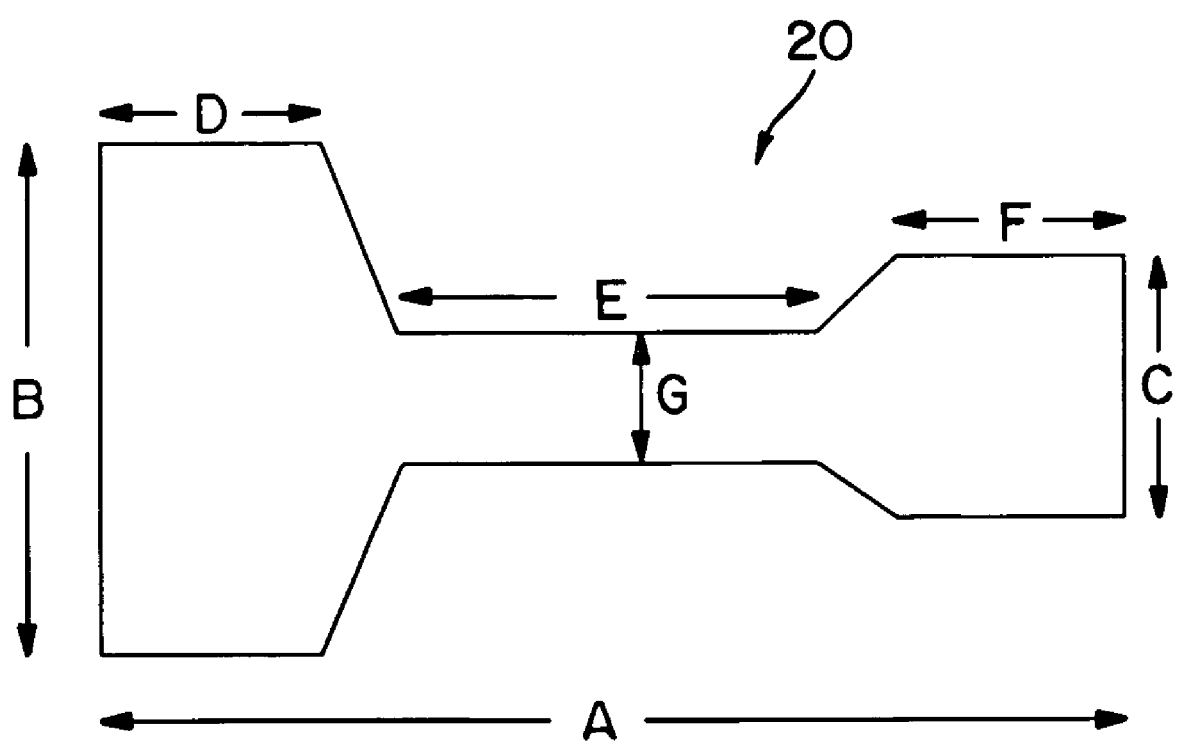
FIG. 6 is a top view of an absorbent structure as described in Example 1.

Additionally, the absorbent structure 20 itself may be cut or formed into a specific shape to redirect internal forces. For example, the shape of the absorbent structure 20 may be formed in a shape similar to an application into which the absorbent structure 20 will be incorporated. One example of such a shape is illustrated in FIG. 6, described in further detail in the Example below.

The first layer 22 or surface 27 is sufficiently absorbent for high fluid intake and expands to a lesser extent than the second layer 24 or surface 28. In certain embodiments, the first layer 22 (or first surface 27) may even shrink in the presence of a liquid. Materials suitable for use in the first layer 22 include nonwoven materials, wetlaid, airlaid, spunbond, meltblown, coform, bonded-carded webs, foams, tissue, netting, including scrim and woven materials, and combinations of any of these materials. One example of a suitable material is a material having a basis weight of about 50 to about 120 grams per square meter (gsm), which includes a through-air-bonded-carded web of a homogenous blend of 60 percent 3 denier type T-256 bicomponent fiber, including a polyester core/polyethylene sheath, and 40 percent 6 denier type T-295 polyester fiber, both commercially available from KoSa Corporation of Salisbury, N.C., U.S.A. Another example of a suitable material may include a material made of 6 denier polyethylene terephthalate (PET) and 6 denier bicomponent binder fibers, having a basis weight of about 50 to about 120 gsm. Additionally, the first layer 22 and/or the second layer 24 may be elastomeric.

Absorbent materials suitable for forming the second layer 24 in the absorbent structure 20 include, for example, polyether-polyurethane foams made hydrophilic by mixing polyols and water with a pre-polymer (as disclosed in U.S. Pat. No. No. 5,591,779 issued to Bleys et al., which is hereby incorporated by reference in its entirety in a manner consistent with the present document). Surfactant can also be added to enhance hydrophilicity, as described in U.S. Pat. No. 4,137,200 issued to Woods et al., which is hereby incorporated by reference in its entirety in a manner consistent with the present document. Such polyether-polyurethane foams are sufficiently elastic in both the dry and wet states, and tend to expand when wet compared to their dry dimensions. The increase in dimensions is typically in the range of about 20% and can be designed to be isotropic in x-y dimensional change.

Superabsorbent materials, including particulates, may be added to these or other materials in the first and/or second layers 22, 24 to provide increased retention capacity as well as an increased change in the swelling behavior of the materials along with the increased osmotic forces generated by the swelling superabsorbent materials. The type of superabsorbent, as well as level of superabsorbent add-on, can be selected to achieve the desired degree of expansion as well as other properties such as capacity. Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Degussa Superabsorber in Greensboro, N.C., U.S.A. Typically, a superabsorbent material is capable of absorbing at least about 10 times its weight of an aqueous solution containing 0.9 weight percent sodium chloride, or at least about 15 times its own weight, or at least about 20 times its own weight, or at least about 25 times its own weight of an aqueous solution containing 0.9 weight percent sodium chloride.

Superabsorbents used in the first and/or second layers 22, 24 can also include alkali metal salts of polyacrylic acids, polyacrylamides, polyvinyl alcohol, ethylene maleic anhydride copolymers, polyvinyl ethers, hydroxypropylcellulose, polyvinyl morpholinone, polymers and copolymers of vinyl sulfonic acid, polyacrylates, polyacrylamides, polyvinyl pyridine, and the like. Other suitable polymers include hydrolyzed acrylonitrile grafted starch, acrylic acid grafted starch, carboxy-methyl-cellulose, isobutylene maleic anhydride copolymers, and mixtures thereof. Further suitable polymers include inorganic polymers such as polyphosphazene and the like. Furthermore, absorbency can be enhanced by foaming with starch-based and cellulose-based components such as wood and/or vegetable fibrous pulp/flour. Current conventional, commercial superabsorbent polymers are typically cross-linked polymers of partially neutralized acrylic acid.

As another example of a suitable material for the second layer 24, Rynel hydrophilic grade foam, available from Rynel Ltd., Inc. of Boothbay, Me., U.S.A., is polyurethane foam (i.e., 600-SA) containing a spontaneous hydrogel superabsorbent material.

Polyurethane foams suitable for forming the second layer 24 may use any of a variety of urethane prepolymers normally employed for reaction to provide an open-cell foam. Examples of suitable hydrophilic urethane prepolymers include, without limitation, isocyanate terminated or capped polyoxyalkylene ethers including polyoxyethylene polyol prepolymers. Other examples of suitable prepolymers are described in U.S. Pat. No. 4,137,200 issued to Woods et al.; U.S. Pat. No. 4,209,605 issued to Hoy et al.; U.S. Pat. No. 2,993,013 issued to Wolfe, Jr.; and U.S. Pat. No. 3,805,532 issued to Kistner, each of which is hereby incorporated by reference in its entirety in a manner consistent with the present document. General procedures for the preparation of prepolymers are described by J. H. Saunders and X. C. Frisch in *Polyurethanes Chemistry and Technology*, Interscience Publishers, John Wiley & Sons, New York, Vol. XVI, Part 2, High Polymer Series, published in 1987, "Foam Systems" pages 7-26, and "Procedures for the Preparation of Prepolymers" pages 26 et seq., which is hereby incorporated by reference in its entirety in a manner consistent with the present document.

Another example of a suitable prepolymer is a toluene diisocyanate (TDI) terminated with polyethylene polyol, available as TREPOL™ from Rynel Ltd., Inc., with less than 6% of the available unreacted NCO groups and a component functionality of 2 or less. HYPOL™ foamable hydrophilic prepolymers are yet another example of suitable prepolymers. HYPOL™ 2000/3000 grade prepolymers are polymeric liquid polyurethanes, are water-activated, are based on TDI, and are available from Dow Chemical Co. in Midland, Mich., U.S.A.

The hydrophilic prepolymer is activated by the aqueous phase for polymerization upon mixing. Surface active agents may be added to the aqueous phase to optimally adjust surface tension, foam formation, and to adjust wettability. Exemplary surfactants include: SCHERCOPOL™ OMS-NA, a disodium monooleamido MEA sulfosuccinate, available from the Scher Chemicals, Inc. in Clifton, N.J., U.S.A., and PLURONIC® F68, a polypropylene glycol nonionic surfactant which is a block copolymer of propylene oxide and ethylene oxide, available from BASF Corporation in Mount Olive, N.J., U.S.A.

At the time that the prepolymer and the aqueous phases are mixed, superabsorbent can be added with rapid mixing to the formulation at loadings of up to about 50% by dry weight of the total polymer formulation. An example of a suitable superabsorbent material is FAVOR® SXM 880 superabsorbent material (SAM), available from Degussa Superabsorber in Greensboro, N.C., U.S.A. Higher loadings of FAVOR® SXM 880 SAM may produce inefficient superabsorbent utilization and an aesthetically unacceptable stiff granulated material. With smaller particle size distributions or other modifications, such as different shapes, higher loadings may be obtained.

The aqueous phase and the prepolymer are suitably mixed together rapidly and vigorously (without degradation) in a ratio by weight of aqueous phase to prepolymer sufficient to result in an appropriate workable viscosity. This ratio may be in a range of about 6:1 to about 400:1, and typically is formulated with minimal water to avoid superabsorbent hydration within the foaming process. The superabsorbent is introduced to the mixed prepolymer at the last process stage just before forming to have minimal exposure to the water used for activating polymerization. The solution may constitute flowable, liquid incipient polyurethane that can be formed to the desired shape and thickness and subsequently cured in situ. The hydrophilic prepolymer is activated to polymerize by the aqueous phase upon mixing. The rheological property of the solution permits automated production. A balanced amount of water in the polymer formulation is used to produce the desired foam and to have viable process conditions. For example, excess water helps to dissipate exothermic heat and to limit the temperature of the reaction but at the same time causes premature hydration and swelling of the superabsorbent material which creates unacceptable foam aesthetics, inefficient superabsorbent material utilization, and drying problems. Use of excess water can also assure that all available isocyanate sites are consumed or reacted. Therefore, the balance between water:prepolymer ratio, process conditions (such as dwell time, mixing, temperature, and the like), and superabsorbent hydration and swelling are carefully adjusted by those skilled in the art to produce the desirable foam.

As another example of a suitable foam for the second layer 24, Rynel hydrophilic grade foam 600-SA, available from Rynel Ltd., Inc., at 2 mm thick and loaded with 25%, by weight, FAVOR® SXM 880 superabsorbent material (SAM), available from Degussa Superabsorber, expands isotropically in the X-Y plane by about 40% when sufficiently wetted with 0.9% NaCl saline. As yet another example, the same foam with a 50%, by weight, loading of FAVOR® SXM 880 SAM expands by about 70%.

Other suitable materials from which the second layer 24 may be formed include, in general, thermoplastic hydrophilic foams, thermoset hydrophilic foams, cellulosic foams, superabsorbent foams, foam materials with superabsorbent particles embedded therein, non-foam materials with superabsorbent particles embedded therein, coforms, staple fiber webs, spunbonds with superabsorbents, meltblowns with superabsorbents, superabsorbent films and scrims, nettings and scrims, superabsorbent-containing fibrous webs of cellulose and/or staple fibers, and/or airlaid, and combinations of any of these. Additionally, any of the above materials with elastic properties are also suitable. Suitably, the materials used to form the second layer 24 have sufficient flexibility, integrity, and elasticity to differentially expand upon wetting to form the desired concavity.

As another example of a suitable material for the second layer 24, an absorbent elastic nonwoven material such as that described in U.S. Pat. No. 6,362,389 may be used. U.S. Pat. No. 6,362,389 issued to McDowall et al., is hereby incorporated by reference in its entirety in a manner consistent with the present document. The level of expansion of this material can be controlled by, among several factors, the amount and type of superabsorbent and elastic filament matrix.

In a single-layer embodiment of the absorbent structure 20, any of the materials described herein as suitable for the second layer 24 may also be suitable for the single-layer absorbent structure.

In certain embodiments, the absorbent structure 20 can be bonded to a secondary relatively fixed member, such as another layer or component of an absorbent article. More particularly, the first surface 27 may be bonded to a liner material, and/or the second surface 28 may be bonded to an outer cover material. Attachment to a relatively fixed member can enhance or diminish the concavity of the absorbent structure 20, depending on which surface (s) is bonded and the properties of the member to which the surface (s) is attached.

The absorbent structure 20 is particularly suitable for use in a variety of absorbent article applications including, without limitation, personal care absorbent articles and medical absorbent articles. Personal care absorbent articles include diapers, training pants, swim wear, absorbent underpants, child-care pants, adult incontinence products including but not limited to pads, containers, incontinence products, and urinary shields, feminine hygiene products including but not limited to sanitary napkins, menstrual pads, panty liners, panty shields, interlabials, tampons, and the like. Medical absorbent articles include medical absorbent garments, drapes, gowns, bandages, wound dressings, underpads, bed pads, and the like. Besides use of such absorbent structures for personal care products and medical absorbent articles, the absorbent structures can also be used in a wide array of applications including but not limited to a variety of cleaning applications, clothing components, filters, athletic and recreation products, and construction and packaging uses.

Figure 7:
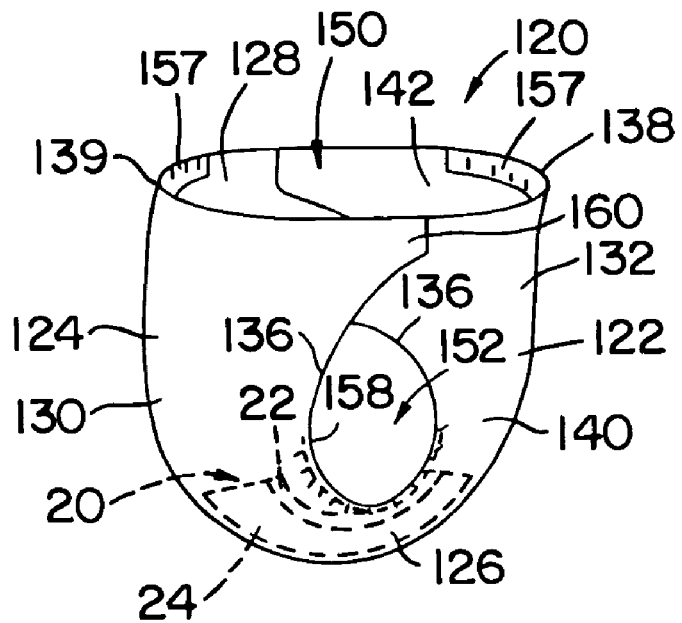
FIG. 7 is a perspective side view of an absorbent article into which an absorbent structure is incorporated.

One example of an absorbent article including the absorbent structure 20 is illustrated in FIG. 7. For ease of explanation, the description of the absorbent article hereafter will be in terms of a diaper 120. The diaper 120 includes a chassis 132. The chassis 132 defines a front region 122, a back region 124, a crotch region 126 interconnecting the front and back regions, a body-contacting surface 128 which is configured to contact the wearer, and an outer surface 130 opposite the body-contacting surface which is configured to contact the wearer's clothing. The front region 122 is contiguous with a front waist edge 138, and the back region 124 is contiguous with a back waist edge 139.

The diaper 120 includes an outer cover 140, a body side liner 142 which is connected to the outer cover 140 in a superposed relation, and the absorbent structure 20 is positioned or located between the outer cover 140 and the body side liner 142. Suitably, the outer surface 28 of the second layer 24 of the absorbent structure 20 may be bonded to the outer cover 140. The design of the diaper 120 must be able to accommodate the wet concavity of the absorbent structure 20. If insufficient room exists within the structure of the diaper 120, then the concavity of the absorbent structure 20 may be inhibited, or may result in undesirable buckling of the absorbent structure 20.

A pair of side panels 160 may be attached to the outer cover 140 and/or the body side liner 142. These side panels 160 can be tabs, straps, tearable seams, or similar devices that can be fastened between the front region 122 and the back region 124 by suitable means, including adhesives, or mechanical means such as VELCRO® hook and loop fasteners, available from Velcro Industries B.V., Amsterdam, Netherlands or affiliates thereof As shown in the diaper 120 in FIG. 7, the front and back regions 122 and 124 together define a three-dimensional pant configuration having a waist opening 150 and a pair of leg openings 152. The waist edges 138 and 139 of the absorbent chassis 132 are configured to encircle the waist of the wearer when worn and provide the waist opening 150 which defines a waist perimeter dimension. Portions of the transversely opposed side edges 136 of the chassis 132 in the crotch region 126 generally define the leg openings 152. The front region 122 includes the portion of the diaper 120 which, when worn, is positioned on the front of the wearer while the back region 124 includes the portion of the diaper 120 which, when worn, is positioned on the back of the wearer. The crotch region 126 of the diaper 120 includes the portion of the diaper 120 which, when worn, is positioned between the legs of the wearer and covers the lower torso of the wearer. The side panels 160 of the diaper 120, when worm, are positioned forward from the hips of the wearer.

To further enhance containment and/or absorption of body exudates, the diaper 120 can include waist elastic members 157 and/or leg elastic members 158, as are known to those skilled in the art (FIG. 7). The waist elastic members 157 can be operatively joined to the outer cover 140 and/or the body side liner 142 along the opposite waist edges 138 and 139, and can extend over part or all of the waist edges. The leg elastic members 158 are desirably operatively joined to the outer cover 140 and/or the body side liner 142 longitudinally along the opposite side edges 136 and positioned in the crotch region 126 of the diaper 120.

The outer cover 140 desirably includes a material that is substantially liquid-impermeable, and can be elastic, stretchable or nonstretchable. The outer cover 140 can be a single layer of liquid-impermeable material, but desirably includes a multi-layered laminate structure in which at least one of the layers is liquid-impermeable. For instance, the outer cover 140 can include a liquid-permeable outer layer and a liquid-impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid-permeable outer layer can be any suitable material and desirably one that provides a generally cloth-like texture. One example of such a material is a 20 gsm (grams per square meter) spunbond polypropylene nonwoven web available from Kimberly-Clark Corporation, Roswell, Ga., U.S.A. The outer layer may also be made of those materials of which liquid-permeable body side liner 142 is made. While it is not a necessity for the outer layer to be liquid-permeable, it is desired that it provides a relatively cloth-like texture to the wearer.

The inner layer of the outer cover 140 can be both liquid and vapor-impermeable, or can be liquid-impermeable and vapor-permeable. The inner layer is desirably manufactured from a thin plastic film, although other flexible liquid-impermeable materials may also be used. The inner layer, or the liquid-impermeable outer cover 140 when a single layer, prevents waste material from wetting articles, such as bedsheets and clothing, as well as the wearer and care giver. A suitable liquid-impermeable film for use as a liquid-impermeable inner layer, or a single layer liquid-impermeable outer cover 140, is a 0.2 millimeter thick polyethylene film commercially available from Huntsman Packaging Corporation of Newport News, Va., U.S.A. If the outer cover 140 is a single layer of material, it can be embossed and/or matte finished, thus providing a more cloth-like appearance. As earlier mentioned, the liquid-impermeable material can permit vapors to escape from the interior of the disposable absorbent article, while still preventing liquids from passing through the outer cover 140. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

The liquid-permeable body side liner 142 is illustrated as overlying the outer cover 140 and absorbent structure 20, and may but need not have the same dimensions as the outer cover 140. The body side liner 142 is desirably compliant, soft feeling, and non-irritating to the wearer's skin. Further, the body side liner 142 can be less hydrophilic than the absorbent structure 20, to present a relatively dry surface to the wearer and permit liquid to readily penetrate through its thickness.

The body side liner 142 can be manufactured from a wide selection of web materials, such as synthetic fibers (for example, polyester or polypropylene fibers, meltblown or spunbond fibers), cellulose fibers (for example, wood or cotton fibers), a combination of natural and synthetic fibers, porous foams, netting, reticulated foams, scrims, apertured plastic films, or. the like. Various woven and nonwoven fabrics can be used for the body side liner 142. For example, the body side liner 142 can be composed of a meltblown or spunbonded web of polyolefin fibers. The body side liner 142 can also be a bonded-carded web composed of natural and/or synthetic fibers. The body side liner 142 can be composed of a substantially hydrophobic material, and the hydrophobic material can, optionally, be treated with a surfactant or otherwise processed to impart a desired level of wettability and hydrophilicity.

The various components of the diaper 120 can be integrally assembled together employing various types of suitable attachment means, such as adhesive, ultrasonic and thermal bonds, or combinations thereof.

Figure 8:
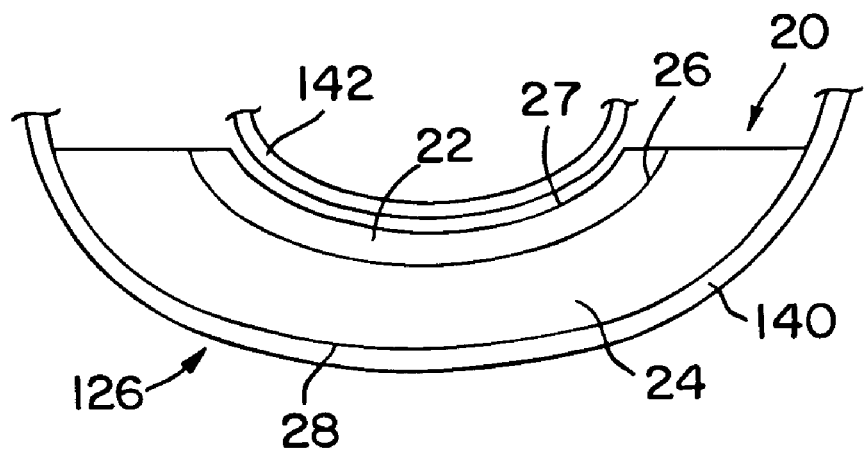
FIG. 8 is an expanded partial view of the crotch region of the absorbent article of FIG. 7.

FIG. 8 illustrates a partial exploded view of the crotch region 126 of the diaper 120 with the absorbent structure 20 incorporated therein.

EXAMPLES

Example 1

Diapers were constructed utilizing an absorbent laminate structure made with a first layer of 2.5 osy (85 gsm) bonded-carded web of about 2 mm thickness laminated to a second layer (about 2-3 mm thick) of polyurethane hydrophilic medical grade foam (600-SA), available from Rynel Ltd., Inc., containing 50% (by weight) of FAVOR® SXM 880 superabsorbent particles, available from Degussa Superabsorber. The lamination was done when the foam was formed, i.e., the foam was contacted with the bonded-carded web prior to completely curing. The absorbent laminate structure had an overall total thickness of about 4 millimeters.

A first diaper was formed by replacing the absorbent structure of a HUGGIES® Ultratrim Step 3 diaper, available from Kimberly-Clark Corporation, Neenah, Wis., U.S.A., with a 3-inch (8-cm) by 12-inch (30-cm) rectangular piece of the absorbent laminate structure with the bonded-carded web side facing towards the spunbond body side liner in order to accept the initial fluid insult. The absorbent laminate structure was glued to an inner surface of the diaper outer cover using hot melt adhesive #7109 from Bostik such that the foam/superabsorbent component of the laminate was bonded to the diaper outer cover.

The rectangular shape of the absorbent laminate structure in the first diaper was intended to produce gasketing and dam effects at the edges and form fluid and solid containment zones in the form of a recessed pocket that is generated in a boat-shape configuration that follows the natural curvature of the body.

The first diaper containing the absorbent laminate structure was tested by fitting it on a baby test mannequin and using a series of four (4) 60 milliliter insults of 0.9% saline applied to the crotch region of the body side liner of the diaper. The mannequin was placed into a walking mode with a walking rate of 60 steps/minute for 15 minutes after each insult. The diaper was examined after each insult. The formation of the desired shape was observed after the initial insult and continued with subsequent insults.

A second diaper was constructed similar to the first diaper but with a shaped absorbent laminate structure having dimensions shown in FIG. 6, wherein the total length (A) was 12 inches (30 cm), the back waist edge width (B) was 4 inches (10 cm), the front waist edge width (C) was 3 inches (8 cm), the back side panel edge length (D) was 3 inches (8 cm), the crotch region length (E) was 4 inches (10 cm), the front side panel edge length (F) was 3 inches (8 cm), and the crotch region width (G) was 2 inches (5 cm). This diaper was tested using the same protocol used for the first diaper. It was observed that the shaping of the core in the second diaper allowed for additional control of the three-dimensional shaping occurring after the first insult and continuing with each insult.

A third diaper was constructed similar to the first diaper but with three longitudinal slits in the foam portion of the absorbent laminate structure to encourage gasketing and contouring of the shape for better fit. The slits were each the full-length of the foam portion (12 inches (30 cm)) of the absorbent laminate structure, with one. slit positioned along the longitudinal centerline of the diaper and the other two slits each positioned 0.5 inch (1.3 cm) on each side of the longitudinal centerline. The slits ran only the full depth of the foam. After testing this diaper using the same protocol used on the first and second diapers, it was observed that the slits promoted growth and retention of the desired shape.

A fourth control diaper, HUGGIES® Ultratrim Step 3 diaper, was tested using the same protocol used on the first, second, and third diapers. It was observed that the control diaper did not produce the desired boat-shape configuration.

Example 2

A polyurethane medical grade hydrophilic foam grade (#562-B) from Rynel Ltd., Inc. was obtained at three different thicknesses—1 mm, 2 mm, and 5 mm. The samples had basis weights of about 100 gsm, 200 gsm, and 500 gsm, respectively. Each of the samples was cut to a 0.625 cm by 2.54 cm rectangular shape.

Each foam sample was laminated to either a 0.5 osy (17 gsm) polypropylene spunbond material (SB) having a thickness of 0.145 mm, available from Kimberly-Clark Corporation in Roswell, Ga., U.S.A., or a 2.25 osy (76 gsm) through-air-bonded-carded web (BCW) having a thickness of about 2 mm. The through-air-bonded-carded web material had a density of 0.04 g/cm$^3$, and was composed of 60% by weight of 6 denier KoSa type T-295 polyester fiber and 40% by weight of 3 denier Chisso ESC-HR6 bicomponent fiber. The polyester fiber is available from KoSa, a business having offices located in Charlotte, N.C., U.S.A., and the bicomponent fiber is available from Chisso Corporation, a business having offices located in Osaka, Japan.

Low-melt, fast-setting, polyester-based adhesive web, Grade PE65@ 50 gsm from Bostik, Inc. in Middleton, Mass., U.S.A., was used to sufficiently bond the two layers together, and bonding conditions were set at 150 degrees Fahrenheit for 15 seconds under sufficient load pressure to instill intimate contact between the two layers yet avoid foam structure destruction or crushing. Upon wetting, the swelling characteristic of the foam by itself was measured to increase about 24% in-plane (X-Y dimensions) and 30% in the thickness (Z-direction).

Aforementioned Equations 1 and 2, above, were used to calculate the estimated radius of curvature and the estimated subtended angle for each sample after exposure to a sufficient amount of 0.9% NaCl saline for full swelling upon hydration. The top layer (SB or BCW) was measured as the dimension of the absorbent structure. The surface of the foam opposite the interface was measured as the expanded dimension.

These samples were fully wetted, swollen, and the subtended angle and the radius of curvature were measured optically. Both the calculated estimates and the actual measurements are presented in Table 1.

TABLE 1

Calculated Estimates and Actual Measurements of Absorbent Laminate Samples

| Top Layer | Bottom Layer | Dry Width, Wc (mm) | Subtended Angle, θ (deg) | Radius of Curvature, R (mm) | Calculated Subtended Angle, θ (deg) | Calculated Radius of Curvature, R (mm) |
|---|---|---|---|---|---|---|
| 17 gsm SB | 5 mm 562-B | 26.1 | 54 | 32.8 | 54 | 34.4 |
| | 2 mm 562-B | 27.5 | 199 | 9.7 | 141 | 13.9 |
| | 1 mm 562-B | 26.0 | 353 | 4.4 | 275 | 6.7 |
| 76 gsm | 5 mm 562-B | 25.6 | 62 | 28.9 | 53 | 34.0 |

TABLE 1-continued

Calculated Estimates and Actual Measurements of Absorbent Laminate Samples

| Top Layer | Bottom Layer | Dry Width, Wc (mm) | Subtended Angle, θ (deg) | Radius of Curvature, R (mm) | Calculated Subtended Angle, θ (deg) | Calculated Radius of Curvature, R (mm) |
|---|---|---|---|---|---|---|
| BCW | 2 mm 562-B | 25.8 | 106 | 15.8 | 132 | 13.9 |
|  | 1 mm 562-B | 25.1 | 170 | 9.4 | 265 | 6.7 |

From Table 1, it can be seen that the calculated radius of curvature and the subtended angle provide good estimates of the actual radius of curvature and the subtended angle. The differences between the actual values and the calculated estimates are primarily due to the simplification and assumptions made in formulating the equations, including the location of the bending beam's neutral axis.

Example 3

In this Example, absorbent samples of various widths were formed using a layer of polyurethane hydrophilic grade foam (600-SA) from Rynel Ltd., Inc. having a thickness of about 2.3 mm and containing 50%, by weight, of FAVORS® SXM 880 superabsorbent material (SAM). The foam layer was formed and layered immediately on a 0.5 osy (17 gsm) through-air-bonded-carded web (BCW) layer having a thickness of about 0.15 mm to form the layered integral structure that had sufficient interfacial bond strength.

The swelling characteristics of the foam were measured separately (~70% planar X-Y dimensional expansion and ~110% thickness or Z-directional expansion), and were used to estimate the subtended angle and radius of curvature of the absorbent laminate samples. Actual measurements of the subtended angle and radius of curvature were also measured when the absorbent laminate samples were in a fully wetted state. As shown in Table 2, the calculated radius of curvature and the subtended angle provide good estimates of the actually observed deformation behavior. The differences in the calculated radius of curvature between the two samples in Table 2 is due to the slight difference in thickness between the two samples.

TABLE 2

Calculated Estimates and Actual Measurements of Absorbent Laminate Samples of Different Widths

| Top Layer | Bottom Layer | Dry Width, Wc (mm) | Subtended Angle, θ (deg) | Radius of Curvature, R (mm) | Calculated Angle, θ (deg) | Calculated Radius of Curvature, R (mm) |
|---|---|---|---|---|---|---|
| 17 gsm BCW | 2 mm 50% SAM | 14.3 | 124 | 10.9 | 125 | 11.2 |
| 17 gsm BCW | 2 mm 50% SAM | 25.9 | 259 | 9.3 | 214 | 11.8 |

Figure 9:
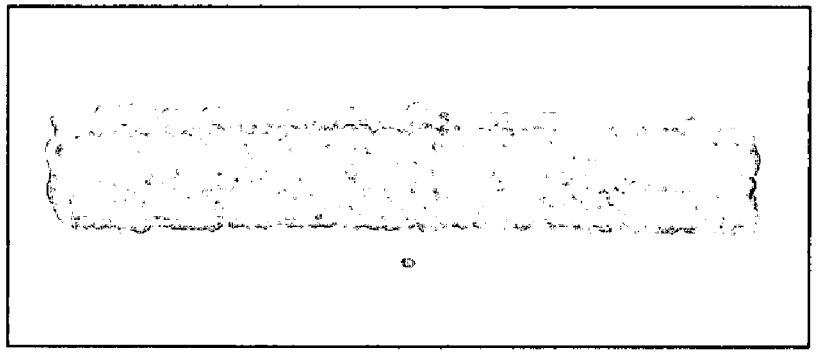
FIGS. 9 and 10 are photographs of the absorbent structure of Example 3 in a dry planar state (FIG. 9) and after hydration and shaping occurs (FIG. 10).
Figure 10:
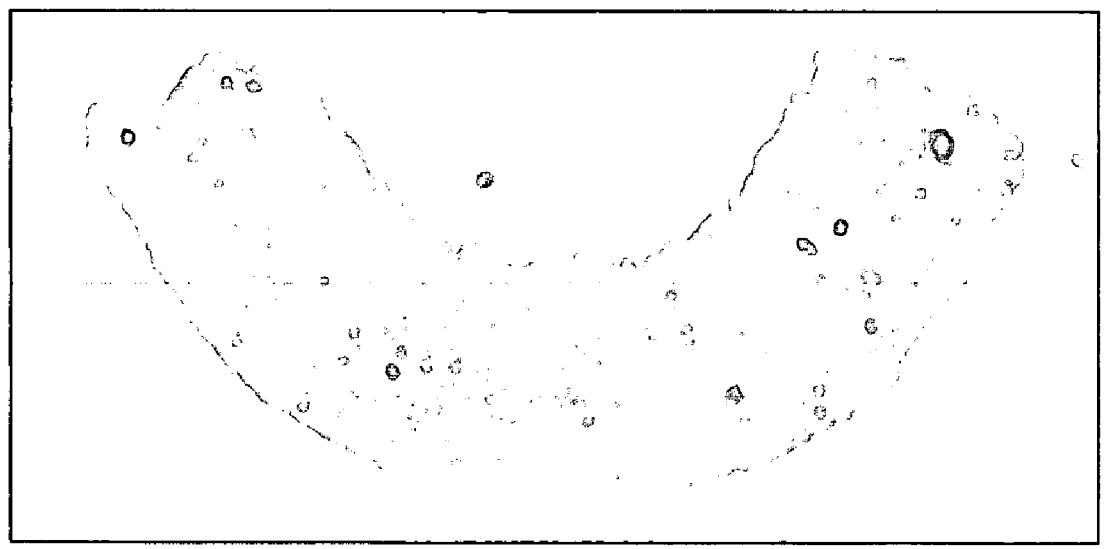

FIGS. 9 and 10 are photographs of the absorbent structure of Example 3 having a width of 14.3 mm. These photographs depict the absorbent structure in a dry planar state (FIG. 9) and after hydration and shaping occurs (FIG. 10).

TEST METHODS

Gurley Stiffness Test Method

A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-E manufactured by Gurley Precision Instruments in Troy, N.Y., U.S.A. For purposes of the present invention, the stated Gurley stiffness values are intended to correspond to the values that would be generated by a "standard" sized sample (1-inch by 1.5-inch). Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

Edge Compression Test Method

The method by which the Edge-wise Compression (EC) value can be determined is set forth below. A 2-inch by 12-inch (5.1 cm by 30.5 cm) piece of absorbent foam is used. The weight of the sample is determined. The thickness of the material is determined under a 0.2 psi (1.38 KA) load. The material is formed into a cylinder having a height of 2 inches (5.1 cm), and with the two ends having 0-0.125 inch (0-3.18 mm) overlap, the material is stapled together with three staples. One staple is near the middle of the width of the product, the other two nearer each edge of the width of the material. The longest dimension of the staple is in the circumference of the formed cylinder to minimize the effect of the staples on the testing.

A tensile tester, such as those commercially available from MTS Systems Corporation in Eden Prairie, Minn., U.S.A., is configured with a bottom platform, a platen larger than the circumference of the sample to be tested and parallel to the bottom platform, attached to a compression load cell placed in the inverted position. The specimen is placed on the platform under the platen. The platen is brought into contact with the specimen and compresses the sample at a rate of 25 mm/min. The maximum force obtained in compressing the sample to 50% of its width (1 inch) (2.54 cm) is recorded.

Buckling of the material is identified as a maximum in the compression force and is typically observed before the material is compressed to 50% of its uncompressed length. In a product where the length of the absorbent is less than 12 inches (30.5 cm), the EC value of the material can be determined in the following manner. Based on theoretical models governing buckling stresses, in the Edge-wise Compression configuration described, the buckling stress is proportional to $E*t^2/(H^2)$ with the proportionality constant being a function of $H^2/(R*t)$ where E is the Elastic modulus, H is the height of the cylinder, R is the radius of the cylinder, and t is the thickness of the material. Expressing the stress in terms of force per basis weight, it can be shown that the parameter that needs to be maintained constant is $H^2/R$. Therefore, for a sample that is smaller than 12 inches (30.5 cm), the largest possible circle should be constructed and its height (width of the sample being cut out) adjusted such that $H^2/R$ equals 2.1 inches (5.3 cm). A detailed discussion of the edge-wise compression strength has been given in *The Handbook Of Physical And Mechanical Testing Of Paper And Paperboard*, Richard E. Mark editor, Dekker, 1983 (Vol. 1).

Liquid Saturation Retention Capacity Test

Figure 11:
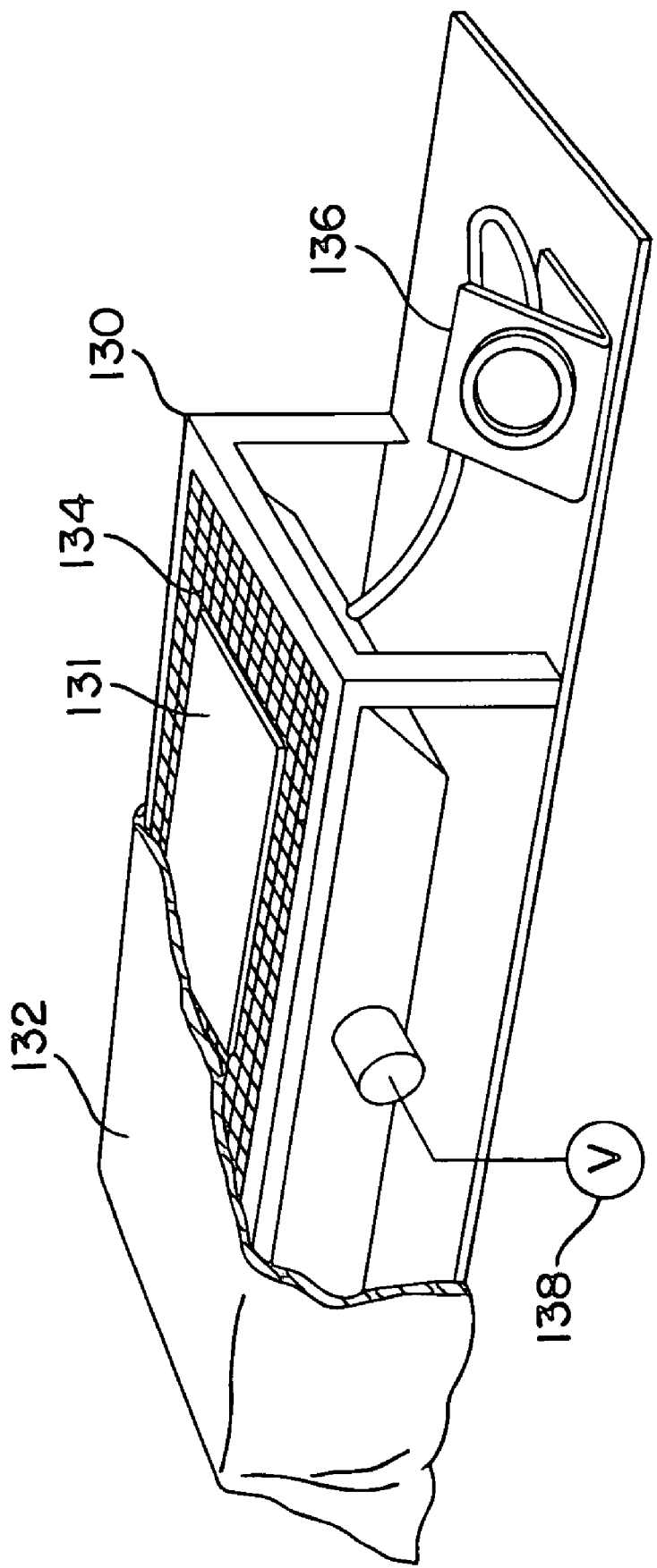
FIG. 11 is an illustration of equipment for determining the liquid saturation retention capacity of an absorbent structure.

The following test is used to determine a retention capacity of an absorbent structure, i.e., the capacity of the absorbent structure for retaining liquid therein. An absorbent structure sample 131 having length and width dimensions of approximately four inches by four inches (approximately 10.16 cm by 10.16 cm) is weighed and the weight in grams is recorded. The sample 131 is then wrapped in toweling (not shown), such as Scott Hi-Dri available from Kimberly-Clark of Neenah, Wis., U.S.A., and submerged in an excess quantity of test solution (i.e., 0.9 weight percent saline solution at about 23 degrees Celsius) for twenty minutes. After this time period, the sample 131 is removed from the test solution and placed on a retention capacity test apparatus, illustrated generally in FIG. 11, comprising a vacuum box 130, a TEFLON fiberglass screen 134 having 0.25 inch (0.6 cm) openings and supported by the vacuum box, and a flexible rubber cover 132 sized for overlaying the screen on the vacuum box.

More particularly, the absorbent structure sample 131 (with toweling) is placed uncovered (e.g., by the rubber cover 132) on the screen 134 and allowed to drip dry for about one minute. The rubber cover 132 is then placed over the sample 131 and screen 134 (e.g., to generally form a seal over the vacuum box 130) and a vacuum (V), drawn by a vacuum pump 138, of about 0.5 pounds/square inch (about 34.5 dynes/square cm), as indicated on a vacuum gauge 136, is drawn on the vacuum box (and hence the sample) for a period of about five minutes. The sample 131 is then removed from the toweling, making an effort to recover loose fibers and superabsorbent particles along with the sample. The recovered sample is again weighed and the weight in grams is recorded. A "total retention capacity" of the sample is determined by subtracting the dry weight of the sample from the weight of the recovered sample after application of the vacuum and is recorded as grams of liquid retained. For relative comparisons to absorbent structures of different mass, a "normalized retention capacity" is determined as the total retention capacity divided by the dry weight of the sample and is recorded as grams of liquid retained per gram of absorbent structure (g/g, or $g_{liq}/g_{abs}$).

If absorbent structure fibers and/or superabsorbent material are drawn through the fiberglass screen into the vacuum box during testing, a screen having smaller openings should be used and the test should be re-done. Alternatively, a piece of tea bag material or other similar material can be placed between the sample and the screen and the total retention capacity adjusted for the liquid retained by the tea bag or other material.

At least three samples of each absorbent structure are tested and the results are averaged to provide the retention capacity (e.g., total and normalized retention capacity) of the absorbent structure.

Fluid Intake Rate Test

Figure 12A:
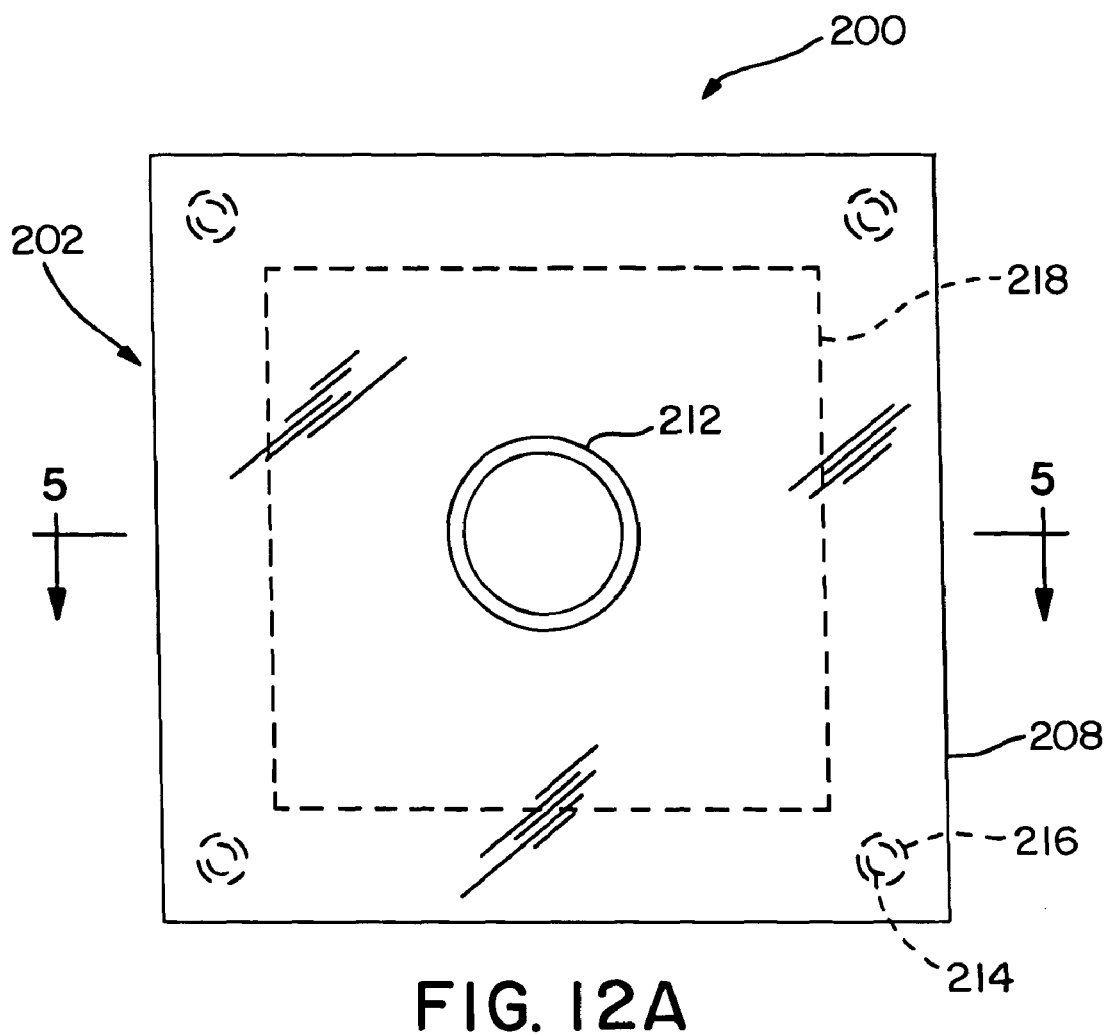
FIGS. 12A-12B representatively show a top view and a side view, respectively, of the test apparatus employed for the Fluid Intake Rate Test.
Figure 12B:
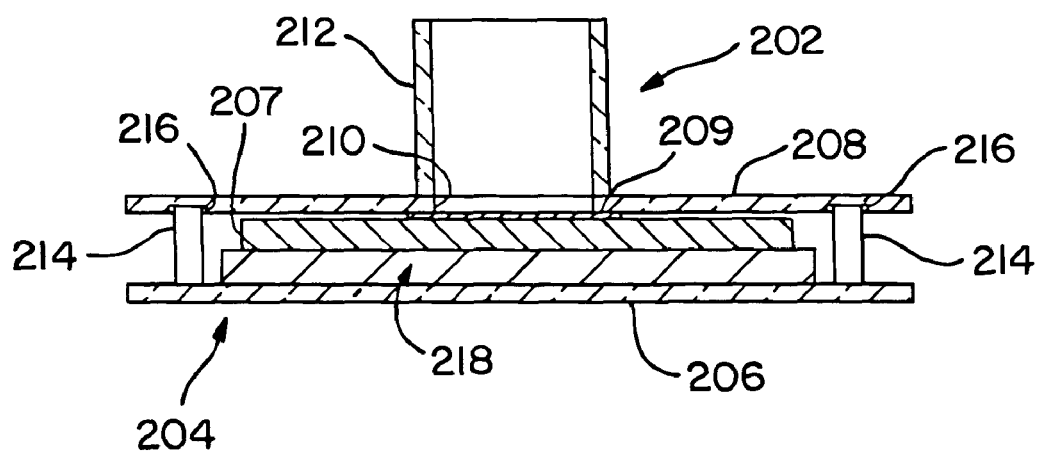

The Fluid Intake Rate (FIR) Test determines the rate at which an absorbent structure takes in (but does not necessarily absorb) a known amount of test solution (0.9 weight percent solution of sodium chloride in distilled water at room temperature). A suitable apparatus for performing the FIR Test is shown in FIGS. 12A and 12B and is generally indicated at 200. The test apparatus 200 comprises upper and lower assemblies, generally indicated at 202 and 204 respectively, wherein the lower assembly comprises a generally 7 inch by 7 inch square lower plate 206 constructed of a transparent material such as PLEXIGLAS® for supporting the absorbent structure sample during the test and a generally 4.5 inch by 4.5 inch square platform 218 centered on the lower plate 206.

The upper assembly 202 comprises a generally square upper plate 208 constructed similar to the lower plate 206 and having a central opening 210 formed therein. A cylinder (fluid delivery tube) 212 having an inner diameter of about one inch is secured to the upper plate 208 at the central opening 210 and extends upward substantially perpendicular to the upper plate. For rate determination, the inside dimension of the fluid delivery tube should maintain a ratio between 1:3 and 1:6 of the sample diameter. The central opening 210 of the upper plate 208 should have a diameter at least equal to the inner diameter of the cylinder 212 where the cylinder 212 is mounted on top of the upper plate 208. However, the diameter of the central opening 210 may instead be sized large enough to receive the outer diameter of the cylinder 212 within the opening so that the cylinder 212 is secured to the upper plate 208 within the central opening 210.

Pin elements 214 are located near the outside corners of the lower plate 206, and corresponding guide-through holes 216 in the upper plate 208 are sized to receive the pin elements 214 to properly align and position the upper assembly 202 on the lower assembly 204 during testing. The weight of the upper assembly 202 (e.g., the upper plate 208 and cylinder 212) is approximately 360 grams to simulate approximately 0.11 pounds/square inch(psi) pressure on the absorbent structure sample during the FIR Test.

To run the FIR Test, an absorbent structure sample 207 being three inches in diameter is weighed and the weight is recorded in grams. The absorbent structure sample 207 is then centered on the platform 218 of the lower assembly 204. The absorbent structure should be oriented in a manner such that the surface expected to contact liquid first or the one that is expected to be facing the user is positioned on top. To prevent unwanted foam expansion into the central opening 210, centered on top of the absorbent structure sample 207, is positioned an approximately 1.5 inch diameter piece of flexible fiberglass standard 18×16 mesh window insect screening 209, available from Phifer Wire Products, Inc., Tuscaloosa, Ala., U.S.A. The upper assembly 202 is placed over the absorbent structure sample 207 in opposed relationship with the lower assembly 204, with the pin elements 214 of the lower plate 206 seated in the guide-through holes 216 formed in the upper plate 208 and the cylinder 212 is generally centered over the absorbent structure sample 207. Prior to running the FIR test, the above-described Saturated Capacity Test is measured on the foam sample 207. Thirty-three percent (33%) of the saturation capacity is then calculated; e.g., if the test material has a saturated capacity of 12g of 0.9% NaCl saline test solution/g of test material and the three-inch diameter absorbent structure sample 207 weighs one gram, then 4 grams of 0.9% NaCl saline test solution (referred to herein as the insult) is poured into the top of the cylinder 212 and allowed to flow down into the absorbent structure sample 207. A stopwatch is started when the first drop of solution contacts the absorbent structure sample 207 and is stopped when the liquid ring between the edge of the cylinder 212 and the absorbent structure sample 207 disappears. The reading on the stopwatch is recorded to two decimal places and represents the intake time (in seconds) required for the first insult to be taken into the absorbent structure sample 207.

An intake rate (in cubic centimeters/second) is determined by dividing the amount of solution (e.g., four grams) used for the insult by the intake time measured for the corresponding insult.

At least three samples of each absorbent structure are subjected to the FIR Test and the results are averaged to determine the intake time and intake rate of the absorbent structure.

While the embodiments of the invention disclosed herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. A single-layer absorbent structure, comprising:
a first surface opposite a second surface, wherein the single-layer absorbent structure lies flat in a dry state and expands along the second surface in the presence of a liquid so that the first surface increases concavity, wherein a pocket-like shape is formed in the presence of the liquid, the single-layer absorbent structure expands to a lesser extent along the first surface than the single-layer absorbent structure expands along the second surface in the presence of the liquid, the single-layer absorbent structure has a fluid intake rate of about 0.5 cubic centimeters per second or greater, and the single-layer absorbent structure has a thickness of about 10 millimeters or less in a dry state.

2. The single-layer absorbent structure of claim 1, wherein the single-layer of absorbent material comprises at least one of the group consisting of thermoplastic foams, thermoset foams, cellulosic foams, superabsorbent foams, foam materials with superabsorbent particles embedded therein, non-foam materials with superabsorbent particles embedded therein, fibrous materials with superabsorbent particles embedded therein, coforms, staple fiber webs, netting, scrims, superabsorbent scrims, superabsorbent films, spunbond with superabsorbents, meltblown with superabsorbents, elastomeric materials, and combinations thereof.

3. The single-layer absorbent structure of claim 1, wherein the single-layer absorbent structure has a subtended angle of about 180 degrees or less in the presence of a liquid.

4. The single-layer absorbent structure of claim 1, wherein the single-layer absorbent structure has a radius of curvature of about 38 centimeters or less in the presence of a liquid.

5. The single-layer absorbent structure of claim 1, wherein the single-layer absorbent structure has a basis weight between about 50 and about 1000 grams per square meter.

6. The single-layer absorbent structure of claim 1, wherein the first surface is treated to expand less in the presence of a liquid relative to the extent to which the second surface expands in the presence of a liquid.

7. The single-layer absorbent structure of claim 1, wherein the first surface is treated by at least one of the group consisting of necking, creping, pleating, aperturing, and mechanical teasing.

8. The single-layer absorbent structure of claim 1, wherein at least one of the first and second surfaces comprises at least one slit to control shaping.

9. The single-layer absorbent structure of claim 1, wherein at least one of the first and second surfaces comprises at least one region of reduced expansion.

10. The single-layer absorbent structure of claim 9, wherein the at least one region of reduced expansion has been modified by at least one of the group consisting of densification, embossment, heat treatment, adhesive bonding, ultrasonic bonding, and combinations thereof.

11. The single-layer absorbent structure of claim 1, wherein at least one of the first and second surfaces undergoes anisotropic expansion in the presence of a liquid.

12. An absorbent structure positioned between a bodyside liner and an outer cover, the absorbent structure, comprising:
a first layer that expands less than 10% in the presence of a liquid, wherein the first layer is positioned adjacent the bodyside liner; and
an absorbent second layer comprising polyurethane foam and having a basis weight between about 100 and about 1000 grams per square meter bonded to the first layer, wherein the absorbent second layer expands at least 20% in the presence of the liquid so that the second layer increases concavity, wherein a pocket-like shape is formed along an interface of the first and second layers in the presence of the liquid, wherein the absorbent second layer is positioned adjacent the outer cover, and the absorbent structure has a fluid intake rate of about 0.5 cubic centimeters per second or greater.

13. The absorbent structure of claim 12, wherein the absorbent structure has a subtended angle of about 30 degrees to about 180 degrees in the presence of a liquid.

14. The absorbent structure of claim 12, wherein the absorbent structure has a radius of curvature of about 38 centimeters or less in the presence of a liquid.

15. The absorbent structure of claim 12, wherein the structure has a thickness of about 1 to about 10 millimeters in a dry state.

16. The absorbent structure of claim 12, wherein at least one of the first and second layers is elastomeric.

17. The absorbent structure of claim 12, wherein the first layer has a basis weight between about 10 and about 150 grams per square meter.

18. The absorbent structure of claim 12, wherein the first layer comprises at least one of the group consisting of nonwoven materials, wetlaid, airlaid, spunbond, meltblown, coform, bonded-carded webs, foams, tissue, netting, scrim, woven materials, and combinations thereof.

19. The absorbent structure of claim 12, wherein the absorbent second layer comprises at least one of the group consisting of thermoplastic foams, thermoset foams, superabsorbent foams, foam materials with superabsorbent particles embedded therein, and combinations thereof.

20. The absorbent structure of claim 12, wherein the absorbent second layer comprises a superabsorbent material.

21. The absorbent structure of claim 12, wherein at least one of the first and second layers comprises at least one slit to control shaping.

22. The absorbent structure of claim 12, wherein at least one of the first and second layers comprises at least one region of reduced expansion.

23. The absorbent structure of claim 22, wherein the at least one region of reduced expansion has been modified by at least one of the group consisting of densification, embossment, heat treatment, adhesive bonding, ultrasonic bonding, and combinations thereof.

24. An absorbent article, comprising:
a body side liner;
an outer cover; and
an absorbent structure comprising polyurethane foam and having a basis weight between about 50 and about 1000 grams per square meter positioned between the body side liner and the outer cover, wherein the absorbent structure includes a first surface opposite a second surface, the second surface of the absorbent structure is bonded to the outer cover, the absorbent structure expands along the second surface in the presence of a liquid so that the first layer increases concavity, wherein a pocket-like shape is formed in the presence of the liquid, the absorbent structure expands to a lesser extent along the first surface than the absorbent structure expands along the second surface in the presence of the liquid, and the absorbent structure has a fluid intake rate of at least about 0.5 cubic centimeters per second or greater.

25. The absorbent article of claim 24, wherein the absorbent structure comprises a single layer of absorbent material.

26. The absorbent article of claim 25, wherein the single layer of absorbent material comprises at least one of the group consisting of thermoplastic foams, thermoset foams, superabsorbent foams, foam materials with superabsorbent particles embedded therein, and combinations thereof.

27. The absorbent article of claim 24, wherein the first surface is a surface of a first layer and the second surface is a surface of an absorbent second layer that is bonded to the first layer, the second layer expands in the presence of a liquid and increases concavity toward the first layer along an interface of the first and second layers in the presence of a liquid, and the first layer expands to a lesser extent than the second layer expands in the presence of a liquid.

28. The absorbent article of claim 27, wherein the first layer comprises at least one of the group consisting of nonwoven materials, wetlaid, airlaid, spunbond, meltblown, coform, bonded-carded webs, foams, tissue, netting, scrim, woven materials, and combinations thereof.

29. The absorbent article of claim 27, wherein the absorbent second layer comprises at least one of the group consisting of thermoplastic foams, thermoset foams, superabsorbent foams, foam materials with superabsorbent particles embedded therein, and combinations thereof.

30. The absorbent article of claim 24, wherein the first surface is treated to expand less in the presence of a liquid relative to the extent to which the second surface expands in the presence of a liquid.

31. The absorbent article of claim 30, wherein the first surface is treated by at least one of the group consisting of necking, creping, pleating, aperturing, and mechanical teasing.

32. The absorbent article of claim 24, wherein the second surface expands at least 20% in the presence of a liquid.

33. The absorbent article of claim 24, wherein the absorbent article comprises at least one of the group consisting of personal care absorbent articles and medical absorbent articles.

34. The absorbent article of claim 24, wherein the absorbent article comprises at least one of the group consisting of diapers, training pants, swimwear, absorbent underpants, child-care pants, adult incontinence products, pads, containers, urinary shields, feminine hygiene products, sanitary napkins, menstrual pads, panty liners, panty shields, interlabials, tampons, medical absorbent garments, drapes, gowns, bandages, wound dressings, underpads, bed pads, cleaning applications, clothing components, filters, athletic and recreation products, construction products, and packaging products.

35. A single-layer absorbent structure, comprising:
a first surface opposite a second surface, wherein the absorbent structure lies flat in a dry state and expands along the second surface in the presence of a liquid so that the first surface increases concavity, wherein a pocket-like shape is formed in the presence of the liquid, the single-layer absorbent structure expands to a lesser extent along the first surface than the single-layer absorbent structure expands along the second surface in the presence of the liquid, the single-layer absorbent structure has a fluid intake rate of about 0.5 cubic centimeters per second or greater, and at least one of the first and second surfaces undergoes anisotropic expansion in the presence of the liquid.

36. An absorbent structure, comprising:
a first layer having a basis weight between about 10 and about 150 grams per square meter that expands less than 10% in the presence of a liquid; and
an absorbent second layer comprising polyurethane foam and bonded to the first layer, wherein the absorbent second layer lies flat in a dry state, wherein the absorbent second layer expands at least 20% in the presence of the liquid so that the second layer increases concavity, wherein a pocket-like shape is formed along an interface of the first and second layers in the presence of the liquid, and the absorbent structure has a fluid intake rate of about 0.5 cubic centimeters per second or greater measured using the Fluid Intake Rate Test.

37. An absorbent structure, comprising:
a first layer that expands less than 10% in the presence of a liquid; and
an absorbent second layer comprising polyurethane foam and bonded to the first layer, wherein the absorbent second layer lies flat in a dry state, wherein the absorbent second layer expands at least 20% in the presence of the liquid so that the second layer increases concavity, wherein a pocket-like shape is formed along an interface of the first and second layers in the presence of the liquid, the absorbent structure has a fluid intake rate of about 0.5 cubic centimeters per second or greater, and only one of the first and second layers is elastomeric.

38. The absorbent structure of claim 12, wherein the absorbent structure lies flat in a dry state.

39. The absorbent article of claim 24, wherein the absorbent structure lies flat in a dry state.

40. The absorbent structure of claim 1, wherein the single-layer absorbent structure comprises a polyurethane foam.

* * * * *